(12) United States Patent
Wulf et al.

(10) Patent No.: US 7,016,032 B2
(45) Date of Patent: Mar. 21, 2006

(54) DEVICE FOR THE CALIBRATION OF AN OPTICAL DETECTION CHANNEL FOR THE TWO-DIMENSIONAL MEASUREMENT OF MULTI-SPECIMEN CARRIERS

(75) Inventors: Juergen Wulf, Ueberlingen (DE); Andreas Fina, Ueberlingen (DE); Michael Eberhard, Uhldingen-Muehlhofen (DE)

(73) Assignee: CyBio AG, Jena (DE)

( * ) Notice: Subject to any disclaimer, the term of this patent is extended or adjusted under 35 U.S.C. 154(b) by 216 days.

(21) Appl. No.: 10/672,114

(22) Filed: Sep. 26, 2003

(65) Prior Publication Data
US 2004/0061852 A1    Apr. 1, 2004

(30) Foreign Application Priority Data
Sep. 30, 2002   (DE) ................................. 102 46 481

(51) Int. Cl.
*G01J 1/10*    (2006.01)
(52) U.S. Cl. .................. 356/243.1; 250/252.1
(58) Field of Classification Search ................ 356/317, 356/318, 417, 243.1; 250/252.1, 458.1, 459.1, 250/461.1, 461.2
See application file for complete search history.

(56) References Cited
U.S. PATENT DOCUMENTS
4,366,118 A    12/1982   Bunce et al.
4,772,453 A    9/1988    Lisenbee
4,945,250 A    7/1990    Bowen et al.
5,567,294 A    10/1996   Dovichi et al.
2004/0036868 A1 *  2/2004  Jones et al. ............. 356/243.1

FOREIGN PATENT DOCUMENTS
DE   41 14 030    9/1992
DE   42 34 075    3/1994
DE   102 36 029.4 8/2002
WO   WO 01/07896  2/2001

* cited by examiner

*Primary Examiner*—F. L. Evans
(74) *Attorney, Agent, or Firm*—Reed Smith LLP

(57) ABSTRACT

The invention is directed to a device for calibrating an optical detection channel for a two-dimensional, spatially dependent measurement of fluorescent or luminescent radiation in multi-specimen carriers. The invention provides a system for calibrating an optical detection channel for a two-dimensional, spatially dependent measurement of fluorescent or luminescent radiation in multi-specimen carriers permitting a highly accurate calibration of the spatial sensitivity distribution of the sensor array in the detection channel. The invention provides a plate-shaped housing, a luminescent foil inside the housing which is arranged parallel to the window so as to cover its surface, a power source and control units which are provided in the housing for controlling the luminescent foil, so that the luminescent foil can be controlled for homogeneous emission of luminescent light through the window of the housing in different intensity levels.

16 Claims, 1 Drawing Sheet

Figure 1:
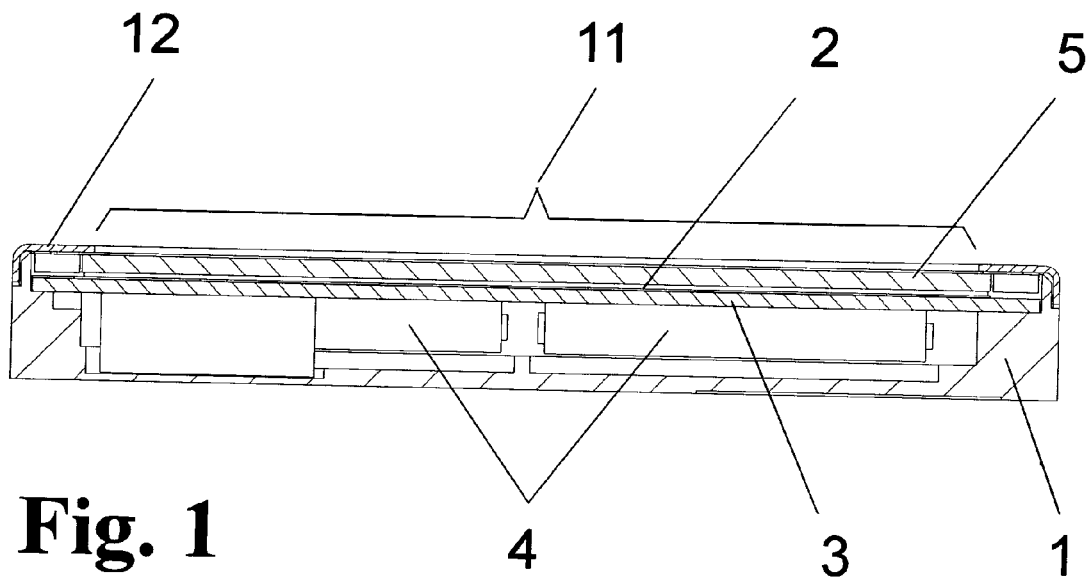

DEVICE FOR THE CALIBRATION OF AN OPTICAL DETECTION CHANNEL FOR THE TWO-DIMENSIONAL MEASUREMENT OF MULTI-SPECIMEN CARRIERS

CROSS-REFERENCE TO RELATED APPLICATION

This application claims priority of German Application No. 102 46 481.2, filed Sep. 30, 2002, the disclosure of which is hereby incorporated by reference.

BACKGROUND OF THE INVENTION a) Field of the Invention

The invention is directed to a device for calibrating an optical detection channel for a two-dimensional, spatially dependent radiation measurement for multi-specimen carriers, particularly microtitration plates (microplates), e.g., for detecting luminescence, fluorescence, phosphorescence or radiation of radioactively labeled assays or for measuring the transmission of such specimens. It is applied especially in optical analysis devices for searching active ingredients in pharmacology and biotechnology.

b) Description of the Related Art

In biochemistry and pharmacology, it is necessary in many cases to test as many different substances as possible in microtitration plates (microplates) within a short period of time by adding reagents or cells. This is usually carried out in the form of an assay in which it is precisely determined at what time the microplate with its specimens must be at what location in what sequence. Usually, the reactions of living cells on substances of pharmacological interest are tested. For this purpose, the cells must be kept in a nutrient medium at a specified temperature and mixed with substances, kept in the incubator again for a defined period of time, etc. But the reverse is also possible, namely, the addition of substances to the wells of the microplate which are charged with reagents or cells.

In many cases, this preparatory handling concludes with optical measurement of luminescence. For this purpose, one or more reagents are added to the cells before or at the moment of measuring the light. Liquid is added to as many (or all) of the wells of the microplate as possible and, further, the light emission is measured simultaneously starting with the addition of liquid. In this connection, there are many competing demands when high plate throughput is to be achieved with automatic HTS (High Throughput Screening) or UHTS (Ultra-High Throughput Screening).

Since the generated light signals are sometimes expected over only a few seconds, a measurement of intensity with a time resolution in the range of seconds per well is required. However, the total measurement time over an entire microplate should be short.

Due to the high cost of the complex compounds of dispensing reagents, only a few microliters ($\mu$l) of a diluted solution may be used on the specimen. This means that a highly sensitive detection system is required.

It is known from U.S. Pat. Nos. 4,772,453 and 4,366,118, for example, to measure the luminescence in microplates successively well by well by means of a photomultiplier (SEV or PMT). A number of solutions for calibration are known (e.g., DE 41 14 030 C1 and DE 42 34 075 C1) for these measurement methods of individual measurement with photomultipliers. However, these solutions are directed only to sensitivity drift over time in detectors of this type because they are concerned exclusively with individual measurements. However, the essential value of eliminating falsification of measured values in order to be able to successfully carry out the intended quantitative substance analysis is clear nonetheless.

Advanced solutions use a highly sensitive CCD camera system for two-dimensional, spatially dependent acquisition of luminescence from microplates. An apparatus of this kind which reads out the luminescence from a microplate by means of a cooled CCD camera is disclosed, for example, in WO 01/07896, in which a Fresnel lens is used as a component of the imaging optics.

A CCD camera is also used in combination with fast optics and preferably with an additional light intensifier in Patent Application DE 102 36 029.4, which was not previously published. However, in spite of the time saved by simultaneous specimen measurement, these luminescence systems which are substantially better suited to the requirements of automatic HTS or UHTS must make do with the disadvantage that the sensitivity of the CCD camera is not homogeneous over the entire surface; in addition, this effect is combined with edge shadows or other imaging errors in the imaging optics used. Because of the low light yield of luminescence coupled with the demanding requirements for quantitative measurement resolution in an assay analysis, these spatially dependent falsifications of measurement values can not be tolerated.

OBJECT AND SUMMARY OF THE INVENTION

It is the primary object of the present invention to find a novel possibility for calibrating an optical detection channel for a two-dimensional, spatially dependent radiation measurement of the individual specimens of multi-specimen carriers which permits a highly accurate calibration of the spatial sensitivity distribution of the sensor array in the detection channel which is economical, can be repeated at any time and can be adapted to the intensity level of the measurement task.

In a device for calibrating an optical detection channel for a two-dimensional, spatially dependent radiation measurement for multi-specimen carriers, particularly microtitration plates, in which the radiation of a plurality of specimens is to be measured photometrically in a darkened measurement chamber, the above-stated object is met, according to the invention, in that the device has a plate-shaped housing which is manufactured in the shape and size of the multi-specimen carrier under examination, in that the housing has, on its side facing the detection channel, a large-area rectangular window whose size is adapted to the surface of the multi-specimen carrier under examination, which surface is provided with wells, and in that there is a luminescent foil inside the housing which is arranged parallel to the window so as to cover its surface, and a power source and control units are provided in the housing for controlling the luminescent foil, so that the luminescent foil can be controlled for homogeneous emission of luminescent light through the window of the housing in different intensity levels.

An electro-luminescent foil is advantageously used as luminescent foil because it can be controlled in a simple manner, particularly with respect to its brightness.

With respect to the radiation of the assay in multi-specimen carriers which is to be measured by the detection channel, the luminescent foil is advisably covered by a filter layer to adjust a required defined bandwidth of the calibrating luminescence and to change it if necessary. In addition to the use of a suitable bandpass filter, the filter layer can also advisably contain a plurality of layers such as a neutral density filter and one or more edge filters.

Further, it is advantageous when the luminescent foil is covered by a pattern mask which simulates a pattern of wells of the multi-specimen carrier under examination. In this way, determined shadows cast by the edges of the wells and the pixels on the receiver matrix which are associated with the position of the wells can be taken into account.

In order to simulate different microplates (with different quantities of wells on the same surface), correspondingly different pattern layers can be used. These pattern layers can be made from an etched plate, an embossed or etched foil or as a light-tight press-on on an existing filter layer (e.g., neutral density filter).

Like all of the layers (e.g., also filter layers) covering the luminescent foil, the pattern layers can advantageously be exchanged in a simple manner when the window is incorporated in a hinged or fold-up cover of the housing. The fold-up cover also makes it possible to exchange elements that are arranged farther inside the housing, which will be discussed in the following.

A storage battery is preferably installed in the housing as power source. In this case, it is advisable that the housing has a charging socket for connecting the power source to an external charging device. The charging socket is advantageously arranged at one of the side surfaces of the housing.

The side surfaces of the housing are advisably provided for arranging additional operator controls such as an on/off switch or a brightness switch. The brightness switch advantageously has a plurality of brightness levels for adjusting the emitted intensity of the luminescent foil. By successive selection of different intensity levels of the radiation of the luminescent foil, the linearity of the detector channel can be defined at least in a wavelength range adjusted by means of the filter layer over an intensity range between the selected intensity levels.

The underlying idea of the invention consists in that a simultaneous two-dimensional photometric measurement of the individual specimens of a multi-specimen carrier with respect to the intensity of generated or transmitted radiation which is relatively weak on the one hand and, on the other hand, must be detected with quantitatively high resolution with respect to the (spatially separated) intensities requires a homogenization of the sensitivity of the detection channel over the entire observed surface of the multi-specimen carrier. However, a one-time measurement of the sensitivity distribution of the utilized CCD chip is not sufficient for this purpose because the spatial sensitivity of the detection channel is influenced by the imaging optics (vignetting and/or distortion) and by diffraction effects and scatter light effects of the different well densities in different multi-specimen carriers. In order to solve this problem, a calibrating device is realized, according to the invention, in the form of conventional multi-specimen carriers to be measured by which, by means of a luminescent foil, a homogeneous luminescent radiation which is controllable with respect to its intensity is generated in the object plane of the detection channel, so that the image elements of the sensor array can be acted upon with respect to their sensitivity by correction values.

By means of the calibrating device according to the invention, it is possible to calibrate an optical detection channel for a two-dimensional, spatially dependent measurement of fluorescent or luminescent radiation of multi-specimen carriers, wherein the device economically permits an accurate calibration of the spatial sensitivity distribution of the sensor array in the detection channel which can be repeated at any time and which can be adapted to the intensity level of the measurement job.

Due to its preferred format (size and shape of microplates), the calibrating device can be used in devices for measuring emitted luminescent, fluorescent or phosphorescent radiation, including the radiation emitted by radioactively labeled assays, and for measuring transmitted light in any optical analysis instruments which are designed for multi-specimen carriers of this type and which carry out a two-dimensional photometric measurement of a plurality of wells by means of receiver arrays (e.g., CCD, or displacement of a line array or of an individual photomultiplier), particularly for active ingredient analysis. It can be used for recalibration by the operator at any time.

The invention will be described more fully in the following with reference to embodiment examples.

BRIEF DESCRIPTION OF THE INVENTION

Figure 2:
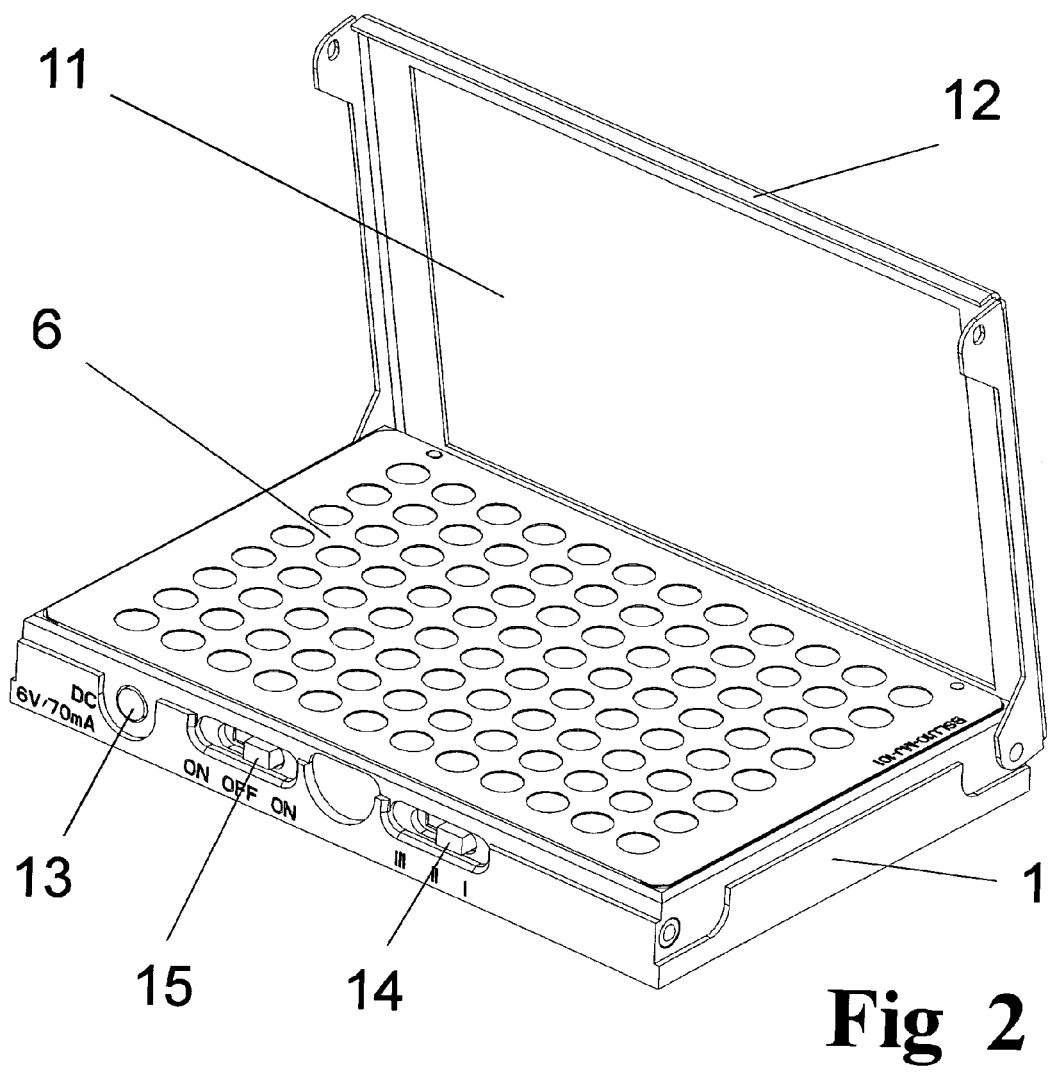

In the drawings:

FIG. 1 shows a schematic view of the device according to the invention in vertical section; and FIG. 2 shows a preferred construction of the calibrating device with fold-up cover.

DESCRIPTION OF THE PREFERRED EMBODIMENTS

In its basic construction as shown in FIG. 1, the calibrating device comprises a plate-shaped housing 1 which is adapted in shape and size to the format of microplates and has a window 11 in one of its parallel surfaces, so that a luminescent foil 2 located inside the housing 1 can emit luminescent radiation. The luminescent foil is controlled by a printed circuit board 3 with storage batteries 4, so that it radiates homogeneously at a selected brightness (intensity) over the surface.

An (exchangeable) filter layer 5 by means of which the spectral range and intensity of the emitted luminescent radiation is limited is arranged above the luminescent foil 2 and is adapted to the bandwidth of the luminescent radiation of the specimens (assays, cell layers, etc.) to be measured by an analysis device in HTS mode. Instead of a filter layer 5 acting as bandpass filter, a plurality of filters, e.g., suitable edge filters and/or neutral density filters, can also be integrated in the filter layer.

The calibrating device can preferably be used with analysis devices for analyzing microplates and the like multi-specimen carriers which have a photometric radiation measurement (with two-dimensional optical detection channel). Device-specific calibrating data records by means of which raw photometric measurement data that have been falsified by influences inherent in the system can be corrected by means of evaluating software can be generated by means of the calibrating device.

Further, optical analysis devices of different manufacturers can be compared with respect to sensitivity and optical errors.

In a particularly advantageous construction, as can be seen from the perspective view in FIG. 2, the surface of the calibrating device provided with the window 11 is constructed as a fold-up cover 12. This provides for particularly simple handling when installing and exchanging internal elements of the calibrating device which are arranged one above the other in the interior of the housing 1, namely, a built-in printed circuit board 3 for controlling the luminescent radiation, a rechargeable battery 4 as power supply, an electro-luminescent foil 2, the filter layer 5 and a pattern layer 6.

The pattern layer 6 is formed in each instance by one of various exchangeable pattern masks by means of which different patterns of wells of any microplate to be measured can be simulated. Etched plates or embossed or etched foils are preferably used as pattern masks. However, it is also possible to arrange the pattern layer 6 on a surface of the filter layer 5 as a light-tight press-on.

Therefore, the calibrating process which serves primarily to determine the sensitivity differences in the detection channel by recording the intensity values of the individual elements (pixels) of the receiver matrix (e.g., CCD) can be used at the same time for determining and storing in a device-specific manner the locations of the anticipated well-oriented radiation (e.g., luminescent radiation) for the measurement process.

Different operator controls are arranged at one of the narrow side surfaces of the device 1 (the front side of the calibrating device in the present example). These operator controls include a charging socket 13 for connecting a charging device (not shown) for charging the battery 4, a brightness switch 14 for controlling the intensity of the luminescence of the luminescent foil 3 and an on/off switch 15 for turning the calibrating device on and off.

Through the selected form of its housing 1, the calibrating device is handled like a standard microplate such as is used for specimen analysis in an analysis device. When the calibrating device is inserted with the connected luminescent foil 3 (on/off switch 15 in the ON position) and preselected intensity of the luminescent radiation (adjusted at brightness switch 14), the analysis device is switched to calibrating mode, so that with homogeneous luminescent emission of the luminescent foil 3 (i.e., with homogeneous intensity distribution in the object plane of the detection channel) different intensity values of pixels of the matrix receiver (CCD) from which correction values can be calculated are measured and stored. These correction values can then be used in the actual measuring process with a microplate charged with specimens for correcting the erroneous raw measurement values.

While the foregoing description and drawings represent the present invention, it will be obvious to those skilled in the art that various changes may be made therein without departing from the true spirit and scope of the present invention.

REFERENCE NUMBERS 1 housing
11 window
12 cover
13 charging socket
14 brightness switch
15 on/off switch
2 luminescent foil
3 printed circuit board
4 storage batteries
5 filter layer(s)
6 pattern layer (pattern mask)

What is claimed is:

1. A device for calibrating an optical detection channel for a two-dimensional, spatially dependent radiation measurement for multi-specimen carriers, particularly microtitration plates, in which the radiation of a plurality of specimens is to be measured photometrically in a darkened measurement chamber, comprising:

a plate-shaped housing which is manufactured in the shape and size of a multi-specimen carrier under examination;

said housing having, on a side facing a detection channel, a large-area rectangular window whose size is adapted to the surface of said multi-specimen carrier under examination;

said surface of said multi-specimen carrier being provided with wells;

a luminescent foil being provided inside said housing which is arranged parallel to said window so as to cover its surface; and a power source and control units being provided in said housing for controlling the luminescent foil, so that the luminescent foil can be controlled for homogeneous emission of luminescent light through the window of said housing in different intensity levels.

2. The device according to claim 1, wherein the luminescent foil is an electro-luminescent foil.

3. The device according to claim 1, wherein the luminescent foil is covered by a filter layer.

4. The device according to claim 1, wherein the luminescent foil is covered by a pattern mask which simulates a pattern of wells of the multi-specimen carrier under examination.

5. The device according to claim 4, wherein the pattern layer is a pattern mask made from an etched plate.

6. The device according to claim 4, wherein the pattern layer is a pattern mask made from an etched or embossed foil.

7. The device according to claim 4, wherein the pattern layer is a pattern mask in the form of a light-tight press-on on a surface of a filter layer.

8. The device according to claim 3, wherein layers covering the luminescent foil can be exchanged in a simple manner.

9. The device according to claim 1, wherein the window is incorporated in a fold-up cover of said housing which makes it possible to exchange elements that are arranged inside said housing.

10. The device according to claim 1, wherein a battery is provided in said housing as power source.

11. The device according to claim 1, wherein said housing has operator controls at its narrow side surfaces.

12. The device according to claim 10, wherein said housing has a charging socket at one of its side surfaces for connecting the power source to an external charging device.

13. The device according to claim 11, wherein said housing has a brightness switch at one of its side surfaces as a control unit for adjusting the irradiated intensity of the luminescent foil.

14. The device according to claim 13, wherein the brightness switch for adjusting the irradiated intensity of the luminescent foil has a plurality of brightness levels, and by successive selection of different intensity levels of the radiation of the luminescent foil the linearity of the detector channel can be defined at least in a wavelength range adjusted by means of a filter layer over an intensity range between the selected intensity levels.

15. The device according to claim 11, wherein said housing has an on/off switch at one of its side surfaces.

16. The device according to claim 4, wherein layers covering the luminescent foil can be exchanged in a simple manner.

* * * * *